United States Patent
Gaessler et al.

(10) Patent No.: US 7,577,353 B2
(45) Date of Patent: Aug. 18, 2009

(54) DEVICE AND METHOD FOR OPTICALLY INSPECTING A SURFACE

(75) Inventors: Joachim Gaessler, Donaueschingen (DE); Christian Konz, Ohningen (DE); Harald Richter, Constance (DE)

(73) Assignee: Intelligente Optische Sensoren Und Systeme GmbH, Radolfzell (DE)

( * ) Notice: Subject to any disclaimer, the term of this patent is extended or adjusted under 35 U.S.C. 154(b) by 429 days.

(21) Appl. No.: 11/644,524

(22) Filed: Dec. 22, 2006

(65) Prior Publication Data
US 2007/0147821 A1 Jun. 28, 2007

(30) Foreign Application Priority Data
Dec. 23, 2005 (DE) .................. 10 2005 061 834

(51) Int. Cl.
*G03B 15/03* (2006.01)
(52) U.S. Cl. .............. 396/155; 356/237.1; 356/237.3; 356/239.7; 356/239.8; 359/663
(58) Field of Classification Search ............... 396/155, 396/164, 182; 359/663
See application file for complete search history.

(56) References Cited

U.S. PATENT DOCUMENTS

| | | |
|---|---|---|
| 2,369,741 A | 2/1945 | Jones et al. |
| 2,418,107 A | 3/1947 | Simmon et al. |
| 3,176,306 A | 3/1965 | Burns |
| 3,227,509 A | 1/1966 | Baker |
| 3,508,066 A | 4/1970 | Agar |
| 3,597,045 A | 8/1971 | Mathisen |
| 3,709,579 A | 1/1973 | Mokosch |
| 3,772,507 A | 11/1973 | Hills |
| 3,815,998 A | 6/1974 | Tietze |
| 3,917,399 A | 11/1975 | Buzawa et al. |
| 3,963,354 A | 6/1976 | Feldman et al. |

(Continued)

FOREIGN PATENT DOCUMENTS

DE 602066 8/1934

(Continued)

OTHER PUBLICATIONS

German Examination Report, dated Aug. 11, 2006.

*Primary Examiner*—W B Perkey
*Assistant Examiner*—Warren K Fenwick
(74) *Attorney, Agent, or Firm*—Knobbe, Martens, Olson & Bear LLP (57) ABSTRACT

The invention generally relates to a compact, inexpensive-to-manufacture, device of few components for optically inspecting a surface and a method for same employing the device. The section of the surface to be investigated is illuminated by a semitransparent mirror and a field lens, employing a telecentric beam path, and at least part of the light reflected or scattered by the surface is imaged onto the entrance pupil of the optics of an electronic camera by the field lens, via the semitransparent mirror. All optical and electronic components, along with a light- and dust-tight housing, are carried on a specially configured mounting block such that they are self-aligning. The method for inspecting a surface involves automatically recording a series of images of the surface under various types of illumination situations. Those images are assembled into an image of the entire section of the surface to be investigated and analyzed using known image-processing methods.

11 Claims, 4 Drawing Sheets

U.S. PATENT DOCUMENTS

| | | |
|---|---|---|
| 4,010,355 A | 3/1977 | Roehrman et al. |
| 4,019,026 A | 4/1977 | Nakanishi et al. |
| 4,062,623 A | 12/1977 | Suzuki et al. |
| 4,167,677 A | 9/1979 | Suzki |
| 4,171,871 A | 10/1979 | Dill et al. |
| 4,215,939 A | 8/1980 | Miller et al. |
| 4,241,389 A | 12/1980 | Heimer |
| 4,315,201 A | 2/1982 | Suzuki et al. |
| 4,352,016 A | 9/1982 | Duffy et al. |
| 4,412,720 A | 11/1983 | Costa |
| 4,419,013 A | 12/1983 | Heimer |
| 4,422,755 A | 12/1983 | Phillips |
| 4,435,732 A | 3/1984 | Hyatt |
| 4,471,385 A | 9/1984 | Hyatt |
| 4,510,673 A | 4/1985 | Shils et al. |
| 4,547,073 A | 10/1985 | Kugimiya |
| 4,560,865 A | 12/1985 | Bergstrom |
| 4,561,722 A | 12/1985 | Smetana |
| 4,600,936 A | 7/1986 | Khoury et al. |
| 4,603,976 A | 8/1986 | Fetzer et al. |
| 4,618,938 A | 10/1986 | Sandland et al. |
| 4,659,220 A | 4/1987 | Bronte et al. |
| 4,672,184 A | 6/1987 | Fujiwara et al. |
| 4,687,304 A | 8/1987 | Piller et al. |
| 4,688,939 A | 8/1987 | Ray |
| 4,790,027 A | 12/1988 | Scherl |
| 4,872,052 A | 10/1989 | Liudzius et al. |
| 4,972,093 A | 11/1990 | Cochran et al. |
| 5,231,536 A | 7/1993 | Wild et al. |
| 5,265,170 A | 11/1993 | Hine et al. |
| 5,351,150 A | 9/1994 | Lichtman et al. |
| 5,379,266 A | 1/1995 | Russell |
| 5,386,481 A | 1/1995 | Hines et al. |
| 5,469,294 A | 11/1995 | Wilt et al. |
| 5,483,348 A | 1/1996 | Komatsu et al. |
| 5,497,234 A | 3/1996 | Haga |
| 5,515,452 A | 5/1996 | Penkethman et al. |
| 5,715,050 A | 2/1998 | Haga |
| 5,737,122 A | 4/1998 | Wilt et al. |
| 5,741,395 A | 4/1998 | Mozelack et al. |
| 5,751,853 A | 5/1998 | Michael |
| 5,764,874 A * | 6/1998 | White .................. 396/155 |
| 5,825,913 A | 10/1998 | Rostami et al. |
| 5,831,738 A | 11/1998 | Hine |
| 5,842,060 A | 11/1998 | White et al. |
| 5,877,899 A | 3/1999 | Stern et al. |
| 5,880,848 A | 3/1999 | Basler et al. |
| 5,894,342 A | 4/1999 | Bacchi et al. |
| 5,923,020 A | 7/1999 | Kurokawa et al. |
| 5,933,521 A | 8/1999 | Pasic |
| 6,039,254 A | 3/2000 | Froese-Peeck et al. |
| 6,075,883 A | 6/2000 | Stern et al. |
| 6,148,120 A | 11/2000 | Sussman |
| 6,239,869 B1 * | 5/2001 | Heuft et al. .............. 356/239.5 |
| 6,265,684 B1 | 7/2001 | Wu |
| 6,330,059 B1 | 12/2001 | Ishiguro et al. |
| 6,633,375 B1 | 10/2003 | Veith et al. |
| 6,661,521 B1 | 12/2003 | Stern |
| 6,697,116 B1 | 2/2004 | Kurokawa et al. |
| 6,862,147 B1 | 3/2005 | Sonstroem |
| 6,867,424 B2 | 3/2005 | Kurosawa et al. |
| 6,870,949 B2 | 3/2005 | Baldwin |
| 7,469,056 B2 * | 12/2008 | Ramm et al. ................. 382/128 |
| 2005/0122509 A1 | 6/2005 | Backhauss |
| 2005/0213795 A1 * | 9/2005 | Sawamura .................. 382/112 |
| 2006/0164649 A1 * | 7/2006 | Rosengaus .................. 356/450 |

FOREIGN PATENT DOCUMENTS

| | | |
|---|---|---|
| DE | 678166 | 3/1935 |
| DE | 1 653 975 | 2/1971 |
| DE | 2 023 404 | 12/1971 |
| DE | 2 354 141 | 5/1974 |
| DE | 26 15 084 | 10/1976 |
| DE | 25 54 086 | 6/1977 |
| DE | 28 02 286 | 7/1978 |
| DE | 27 18 040 | 10/1978 |
| DE | 28 11 707 | 2/1979 |
| DE | 28 50 957 | 5/1979 |
| DE | 28 51 750 | 3/1980 |
| DE | 30 21 448 A 1 | 6/1980 |
| DE | 28 55 799 | 7/1980 |
| DE | 29 31 668 | 2/1981 |
| DE | 30 29 827 | 2/1981 |
| DE | 30 33 260 A1 | 3/1981 |
| DE | 30 2 1448 A1 | 12/1981 |
| DE | 31 26 197 A1 | 1/1983 |
| DE | 32 31 265 A1 | 2/1984 |
| DE | 32 42 219 C1 | 2/1984 |
| DE | G 84 01 016.9 | 4/1984 |
| DE | 33 18 011 A1 | 11/1984 |
| DE | 34 01 527 A1 | 8/1985 |
| DE | 34 05 634 A1 | 8/1985 |
| DE | 34 22 143 A1 | 12/1985 |
| DE | 35 12 615 A1 | 10/1986 |
| DE | 35 17 070 A1 | 11/1986 |
| DE | 36 37 477 A1 | 5/1988 |
| DE | 36 41 258 A1 | 6/1988 |
| DE | 38 26 317 | 8/1988 |
| DE | 37 07 979 A1 | 9/1988 |
| DE | 37 09 500 A1 | 10/1988 |
| DE | 37 17 274 A1 | 12/1988 |
| DE | 291 153 | 6/1991 |
| DE | 38 87 578 T2 | 5/1994 |
| DE | 37 50 174 T2 | 11/1994 |
| DE | 690 10 318 T2 | 1/1995 |
| DE | 44 34 699 A1 | 4/1996 |
| DE | 195 11 195 A1 | 10/1996 |
| DE | 195 11 196 A1 | 10/1996 |
| DE | 195 11 197 A1 | 10/1996 |
| DE | 197 41 545 A1 | 3/1999 |
| DE | 198 50 144 A1 | 5/2000 |
| DE | 199 03 486 A1 | 8/2000 |
| DE | 199 17 082 A1 | 11/2000 |
| DE | 100 30 772 A1 | 10/2001 |
| DE | 100 45 245 A1 | 3/2002 |
| DE | 101 24 347 A1 | 10/2002 |
| DE | 696 26 851 T2 | 9/2003 |
| DE | 102 37 477 A1 | 11/2003 |
| DE | 102 32 781 A1 | 2/2004 |
| DE | 696 31 342 T2 | 11/2004 |
| DE | 103 23 139 A1 | 12/2004 |
| DE | 103 24 474 A1 | 12/2004 |
| DE | 103 30 003 A1 | 2/2005 |
| DE | 103 59 723 A1 | 7/2005 |
| EP | 0 031 973 | 7/1981 |
| EP | 0 183 946 A2 | 6/1986 |
| EP | 0 217 118 | 4/1987 |
| EP | 0 240 078 A1 | 10/1987 |
| EP | 0 275 469 A2 | 7/1988 |
| EP | 0 312 298 A2 | 4/1989 |
| EP | 0 510 108 B1 | 10/1992 |
| EP | 0 685 140 B1 | 12/1995 |
| EP | 0 689 700 B1 | 1/1996 |
| EP | 0 704 693 A1 | 4/1996 |
| EP | 0 735 361 A2 | 10/1996 |
| EP | 0 924 748 A2 | 6/1999 |
| EP | 0 933 953 A1 | 8/1999 |
| EP | 1 235 268 A1 | 8/2002 |
| EP | 1 291 900 | 3/2003 |
| EP | 1 494 017 A1 | 1/2005 |
| GB | 9 81 431 | 1/1965 |
| GB | 1 047 603 | 11/1966 |
| GB | 1 129 311 | 10/1968 |

| | | | | | | |
|---|---|---|---|---|---|---|
| GB | 1 129 312 | 10/1968 | | WO | WO 91/10968 | 7/1991 |
| GB | 1 135 983 | 12/1968 | | WO | WO 93/13529 | 7/1993 |
| GB | 1 413 723 | 11/1975 | | WO | WO 94/19908 | 9/1994 |
| GB | 1 552 013 | 9/1979 | | WO | WO 95/19012 | 7/1995 |
| GB | 1 559 666 | 1/1980 | | WO | WO 95/35506 | 12/1995 |
| GB | 2 039 030 A | 7/1980 | | WO | WO 97/19416 | 5/1997 |
| GB | 1 575 165 | 9/1980 | | WO | WO 97/24607 | 7/1997 |
| GB | 2 065 914 A | 7/1981 | | WO | WO 97/29593 | 8/1997 |
| GB | 2 139 753 A | 11/1984 | | WO | WO 97/39416 | 10/1997 |
| GB | 2 147 411 A | 5/1985 | | WO | WO 98/10366 | 3/1998 |
| GB | 2 150 314 A | 6/1985 | | WO | WO 98/52088 | 11/1998 |
| GB | 2 361 086 A | 10/2001 | | WO | WO 98/59313 | 12/1998 |
| GB | 2 413 859 A | 11/2005 | | WO | WO 99/62263 | 12/1999 |
| JP | 5616804 | 2/1981 | | WO | WO 02/40976 A2 | 5/2002 |
| JP | 56 126749 | 10/1981 | | WO | WO 03/027630 A2 | 4/2003 |
| JP | 57-112036 | 7/1982 | | WO | WO 03/027630 A3 | 4/2003 |
| JP | 2 198347 | 8/1990 | | WO | WO 2004/010114 A2 | 1/2004 |
| JP | 5-227468 | 9/1993 | | WO | WO 2004/072629 | 8/2004 |
| JP | 8-172506 A | 7/1996 | | WO | WO 2004/072629 A1 | 8/2004 |
| JP | 2002 67275 | 3/2002 | | WO | WO 2004/077336 A2 | 9/2004 |
| WO | WO 84/01024 | 3/1984 | | WO | WO 2004/077336 A3 | 9/2004 |
| WO | WO 84/01212 | 3/1984 | | | | |
| WO | WO 84/03142 | 8/1984 | | * cited by examiner | | |

DEVICE AND METHOD FOR OPTICALLY INSPECTING A SURFACE

CROSS-REFERENCE TO RELATED APPLICATIONS

This Application claims the benefit of German Application DE 10 2005 061 834.0 filed Dec. 23, 2005, which is hereby incorporated by reference in its entirety.

BACKGROUND OF THE INVENTION

1. Field of the Invention

This invention relates generally to a device and a method for optically inspecting a surface.

2. Description of the Related Art

Image recording devices for imaging defects on a planar, reflective surface are known in the art. For example, U.S. Pat. No. 6,870,949 discloses such a device where the section of a surface to be investigated is imaged by a camera, employing a telecentric beam path, and the dark-field illumination of the surface is provided by an annular light source arranged coaxially with respect to the camera's optical axis. It also provides that light from the light source employed for illuminating the surface is normally reflected to the camera's optical axis by a semitransparent mirror, in which case, a bright-field illumination of the surface might also be implemented. The image of the surface to be investigated is thus imaged onto the camera's optics by the field lens and the beam path transits the plane-parallel substrate of the semitransparent mirror, which in turn will likely create image-degrading astigmatism, particularly in cases where the beam has a large divergence angle, such as where the field lens has a short focal length.

U.S. Pat. No. 4,561,722 discloses a beamsplitter for an illuminator-and-sensor-side telecentric beam path that provides for at least a transparent masking of the semitransparent mirror in order to prevent stray-light effects due to the presence of contamination.

Japanese Published Patent Application JP08172506A discloses a manuscript reading device having a camera and nearly on-axis, dark-field illumination, where the same telecentric optics are employed for illumination and configuring the camera's beam path. The nearly on-axis, dark-field illumination yields benefits in terms of the better legibilities of characters, particularly in the case of manuscripts printed on glossy paper.

U.S. Pat. No. 6,870,949 and Japanese Published Patent Application JP 08172506A disclose arrangements involving a camera whose lens lies on the optical axis of the telecentric field lens. These arrangements have the disadvantage that the overall heights of the arrangements, measured along the optical axis of the field lens, increase the focal length of the field lens by an amount equaling the overall length of the camera and its lens.

German Patent DE2354141A1 discloses a device and a method for investigating the planarities of reflective surfaces, where a single point light source is arranged on the optical axis of a field lens. A camera creates an image from which the inclination of the normal vector to the surface to be investigated relative to the optical axis of the field lens is derived. In cases where textures and/or symbols on a reflective surface are to be measured, the device having a point light source has the disadvantage that the illumination will be highly inhomogeneously distributed over the surveyed field for extremely slight inclinations of the optical axis of the path of the illuminating beam relative to the normal to the surface to be investigated, and detection of the textures and/or symbols involved will be severely impaired.

U.S. Pat. No. 4,241,389A discloses a device that creates a number of virtual light sources in the focal plane of a telecentric beam path for the purpose of illuminating a projection mask, employing the Köhler method.

It is an object of the present invention to overcome or ameliorate at least one of the disadvantages of the prior art, or to provide a useful alternative.

SUMMARY OF THE INVENTION

One of the problems addressed by the invention is creating both a compact and inexpensively manufactured device of few components for optically inspecting essentially rectangular sections of diffusely or specularly reflecting surfaces and employing a telecentric beam path. The invention also addresses a method for inspecting such surfaces employing such a compact inspection device, where the dimensions of that device should be substantially minimal, particularly as measured along the optical axis of the field lens. In particular, the term "optically inspecting" is a broad term and shall have its ordinary meaning and shall include, but not be limited to, both detection of surface-texture quality and/or flaws and recognition of symbols and/or encodings.

The preferred embodiments of the device and method of the present invention have several features, no single one of which is solely responsible for their desirable attributes. Without limiting the scope of this invention, its more prominent features will now be discussed briefly. However, not all of the following features are necessary to achieve the advantages of the device and method. Therefore, none of the following features should be viewed as limiting. After considering this discussion, and particularly after reading the section entitled "Detailed Description of the Preferred Embodiments," one will understand how the features of the preferred embodiments provide advantages over prior art devices.

In one aspect, the preferred embodiments of the present invention provide a device for optically inspecting a substantially rectangular investigated section of a specularly or diffusedly reflecting surface having at least one light source for providing bright-field illumination that is imaged onto the investigated section employing a telecentric beam path, an electronic camera having a lens that receives part of the light coming from within the investigated section of the surface via a telecentric beam path and transmits the images obtained to a processor, and an electronic controller for controlling the illumination of the investigated section and the operation of the camera, characterized in that the camera-and-illuminator-side beam path has an aspherical field lens whose focal length is less than twice the maximum dimension of the investigated section, and whose projection on the surface to be investigated at least just barely covers the investigated section, wherein the investigated section is imaged onto the entrance pupil of the lens of the camera by a beam splitter arranged at an angle of about 45° to the optical axis of the field lens and a light source, other than a point source, whose minimum dimension in the focal plane of the field lens equals two to ten times the diameter of the entrance pupil of the lens of the camera is arranged in the focal plane, which is penetrated by the optical axis of the field lens.

In one embodiment, the device is characterized in that the light source that is other than a point source is configured in the form of a ground-glass plate arranged in the focal plane, symmetrically disposed about the optical axis of the field lens, that is illuminated by a lamp arranged behind the focal plane so as to be arranged on that side thereof that faces away from the field lens. In another embodiment, the device is characterized in that the lamp is configured from at least one light-emitting, semiconductor diode. In yet another embodiment, the device is characterized in that the lamp is configured from three LEDs that emit in the red, green, and blue spectral ranges, respectively, and are independently controllable by the controller such that light of various colors may be generated by additive color mixing.

In yet another embodiment, the device is characterized in that at least one additional light source in the form of a linear LED-array is arranged on the illuminator side of the field lens, in the vicinity of the optical axis of the field lens, wherein every such light source is situated behind, as viewed from the field lens, the focal plane, at a distance therefrom equaling at least 15% of the focal length of the field lens, and wherein said light source is controllable by a controller and may be optionally operated either independently of, or jointly with, the light source employed for generating the bright-field illumination.

In another aspect, the preferred embodiments of the present invention provide a method for optically inspecting a substantially rectangular investigated section of a specularly of diffusedly reflecting surface, employing a device having numerous, substantially identical light sources situated in the focal plane of a field lens that are imaged onto the investigated section, employing a telecentric beam path, an electronic camera having a lens that receives part of the light coming from within the investigated section of the surface via telecentric beam path and a beam splitter and transmits the images obtained to a processor, along with an electronic controller for controlling the light sources situated in the focal plane of the field lens and the operation of the camera and a frame buffer and processing circuitry, characterized by the following processing steps: preparing a series of recorded images and storing the recorded images in a frame buffer, wherein each recorded image is characterized by illumination by a group of light sources comprising a fixed number of individual, neighboring light sources from among the numerous light sources, and the light sources have been independently activated and deactivated in sequence, processing individual recorded images stored in the frame buffer and processing circuitry such that the recorded image having the best average brightness will be determined and the associated group of light sources defined as the central bright-field light source for the particular set of investigative conditions involved. The process further includes classifying the groups of light sources into bright-field light sources that include at least the central bright-field light source and, optionally, light sources that are immediately adjacent thereto, and dark-field light sources that are arranged about the bright-field light sources, at distances therefrom equaling at least the lateral dimension of a light source, recording a series of images of the investigative section, wherein the respective illumination conditions employed in recording the images involved range from strictly bright-field illumination, through combined bright-field/dark-field illumination, to strictly dark-field illumination, and processing the recorded images of the investigated section using software that will allow automatically accomplishing the inspection task involved.

In one embodiment, the present invention provides a method for optically inspecting an essentially rectangular investigated section of a specularly or diffusely reflection surface, employing a device according to the preferred embodiments of the present invention, characterized by the following processing steps: preparing a series of recorded images and storing the recorded images in a frame buffer, wherein each recorded image is characterized by differing, intense illumination by the light source that is other than a point source, processing the individual recorded images stored in the frame buffer and processing circuitry such that, from among those recorded images, exclusively those respective portions of the images of the investigative section that have adequate brightness and contrast will be selected for further processing and assembled into a single, processable image, and processing the assembled image of the investigated section, employing software that will automatically accomplish the inspection task involved.

In another embodiment, the present invention provides a method for optically inspecting an essentially rectangular investigative section of a specularly or diffusely reflection surface, employing a device according to the preferred embodiments, characterized by the following processing steps: preparing a series of recorded images and storing those recorded images in a frame buffer, wherein each recorded image is characterized by illumination of the investigated section employing the LED as the light source that is other than a point source and the linear LED-array, and by differing ratios of the intensity of the LED to the intensities of the linear arrays, processing the individual recorded images stored in the frame buffer and processing circuitry such that, from among those recorded images, exclusively those respective portions of the images of the investigative section that have adequate brightness and contrast will be selected for further processing and assembled into a single, processable image, processing the assembled image of the investigated section, employing software that will automatically accomplish the inspection task involved.

In yet another embodiment, the present invention provides a method for aligning a device according to certain preferred embodiments characterized in that the intensity of the LED employed as the light source that is not a point source is set to its maximum tolerated value and the user sets up the device, under visual control, such that the section of the surface that is brightly illuminated by the LED encompasses the investigated section in order to mechanically align the device on the essentially rectangular investigated section.

DETAILED DESCRIPTION OF THE PREFERRED EMBODIMENT

Certain preferred embodiments of the present invention provide a system for optically inspecting an investigated section of a specularly or diffusely reflecting surface. As it will be described in greater detail below, light leaving the surface to be investigated is imaged onto the entrance pupil of the lens of an electronic camera by an aspherical field lens having a short focal length via a semitransparent mirror. In the case of bright-field illumination, the surface is illuminated by a light source, other than a point source, arranged in the focal plane of the field lens, in the vicinity of the field lens' optical axis, which is preferably configured in the form of a ground-glass plate irradiated by a tunable, multicolor, semiconductor light source.

Figure 1:
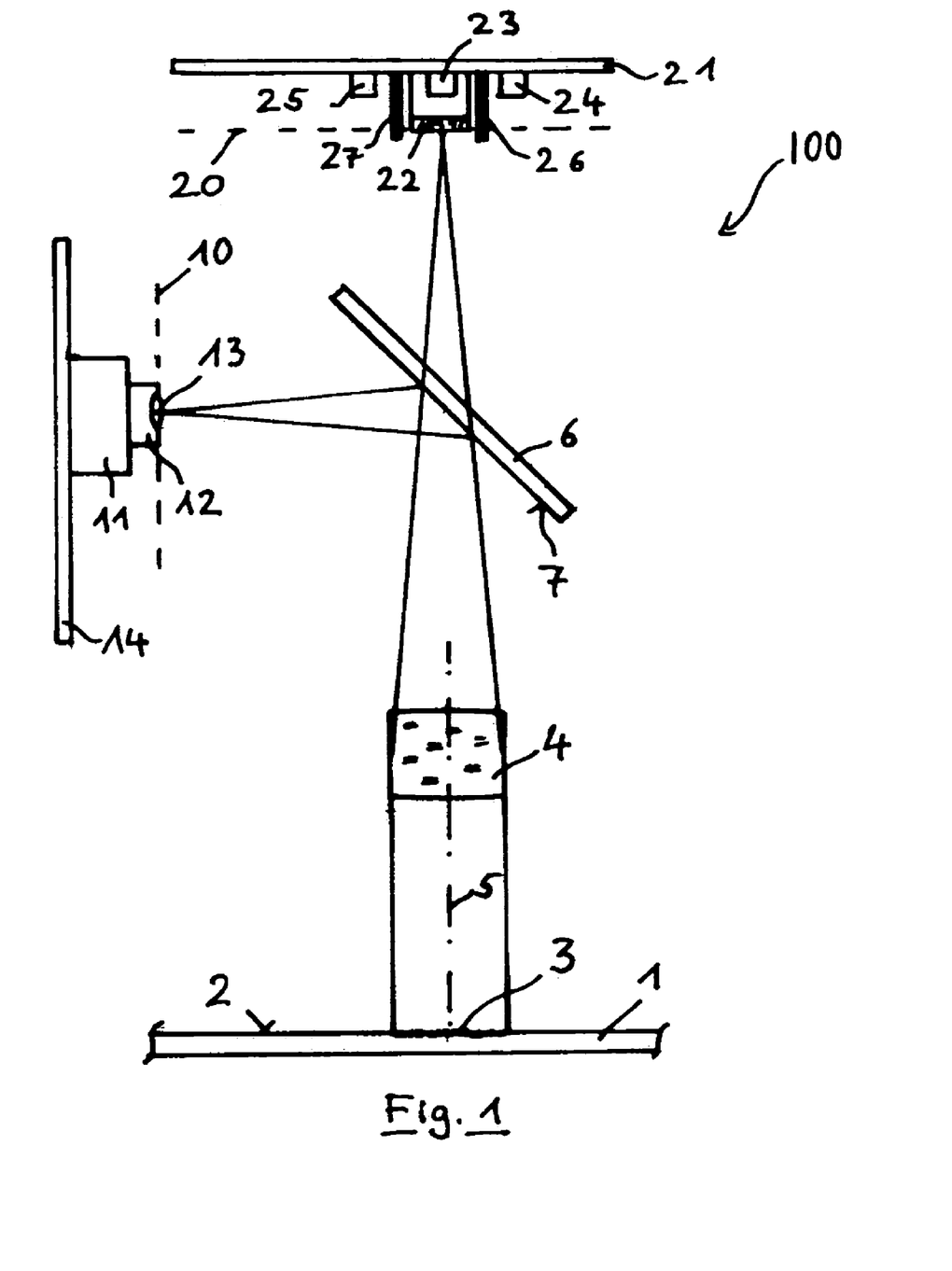
FIG. 1 provides a schematic view of an optical inspection system of one preferred embodiment of the present invention, as viewed normal to the optical axes of the camera lens and field lens.

FIG. 1 schematically illustrates an optical inspection system 100 of one preferred embodiment of the present invention. The system 100 generally includes a camera 11, an aspherical field lens 4, a beamsplitter 6 having a semi-transparent, reflective coating 7, and a light source 23, 24, 25. The system 100 is positioned above an investigated section 3 on an upper surface 2 of a substrate 1. When viewed along the optical axis 5, the field lens 4, which is shown sectioned, has a rectangular cross-section whose dimensions preferably exceed those of the investigated section 3 by a few percent, such as between 1% to 10%, along all axes. A unique feature of the telecentric beam path is that the field lens 4 yields a collimated beam on the side facing the investigated section 3, which means that its projection along the optical axis thus encompasses the investigated section 3. The resultant telecentric imaging optics images the textures of the investigated section 3 at constant magnification, regardless of the distance between the field lens 4 and the surface 2. Telecentric imaging optics are thus preferably employed in optical metrology. In order to arrive at a short overall length, measured along the optical axis 5 of the field lens 4, the divergence angle of the telecentric beam is preferably chosen to be as large as feasible. Since large divergence angles can cause severe imaging errors in the case of optical trains containing spherical optical components, it is contemplated that the field lens 4 be configured in the form of an aspherical lens. In one embodiment, the field lens 4 is ground from glass such that it has at least one aspherical surface and then edged to yield a rectangular shape. It is also contemplated that the field lens 4 can be fabricated by injection molding a plastic material, where at least one surface of the injection-molding die for the field lens 4 is aspherical. In practice, it has been found that aspherical single lenses whose figures have been computed for one wavelength yield sufficiently good imaging properties of the entire system. Light transmitted by the investigated section 3 parallel to the optical axis 5 of the field lens 4 is imaged onto the focal plane 10 of the field lens 4 by the beamsplitter 6 that is arranged at about 45° angle to the optical axis of the field lens 4 and has a semitransparent, reflective coating 7. The entrance pupil 13 of the lens 12 of the camera 11 is arranged in the focal plane 10 such that an object point on the surface 2 lying on the optical axis 5 of the field lens will be imaged onto the center of the entrance pupil 13. The camera 11 employed is preferably an electronic camera having a CCD or CMOS focal-plane device that is arranged on a camera board 14. The camera board 14 preferably contains an electronic circuit for controlling the camera 11, in particular, for controlling image-recording and image-readout operations.

The light source for the bright-field illumination of the investigated section 3 is arranged in the focal plane 20 of the field lens 4, on the extended optical axis 5 of the field lens 4. In one embodiment, the light source has a lateral extension of about 3 mm to 10 mm relative to the optical axis 5 of the field lens 4, and is thus significantly larger than a point source. It is contemplated that a ground-glass plate 22 that is illuminated by a lamp from that side thereof that faces away from the field lens 4 be arranged in the focal plane 20. The lamp employed is preferably a tunable, multicolor, light-emitting diode (LED). Having a light source that is significantly larger than a point source in the focal plane 20 yields the benefit that the condition for bright-field illumination will still be met even when, in the case of a specularly reflecting surface 2, the optical axis 5 of the field lens 4 fails to coincide with the normals to the surface 2, because, for example, the substrate 1 has either not been accurately aligned on the device, or the substrate 1 exhibits departures from planarity.

Figure 2:
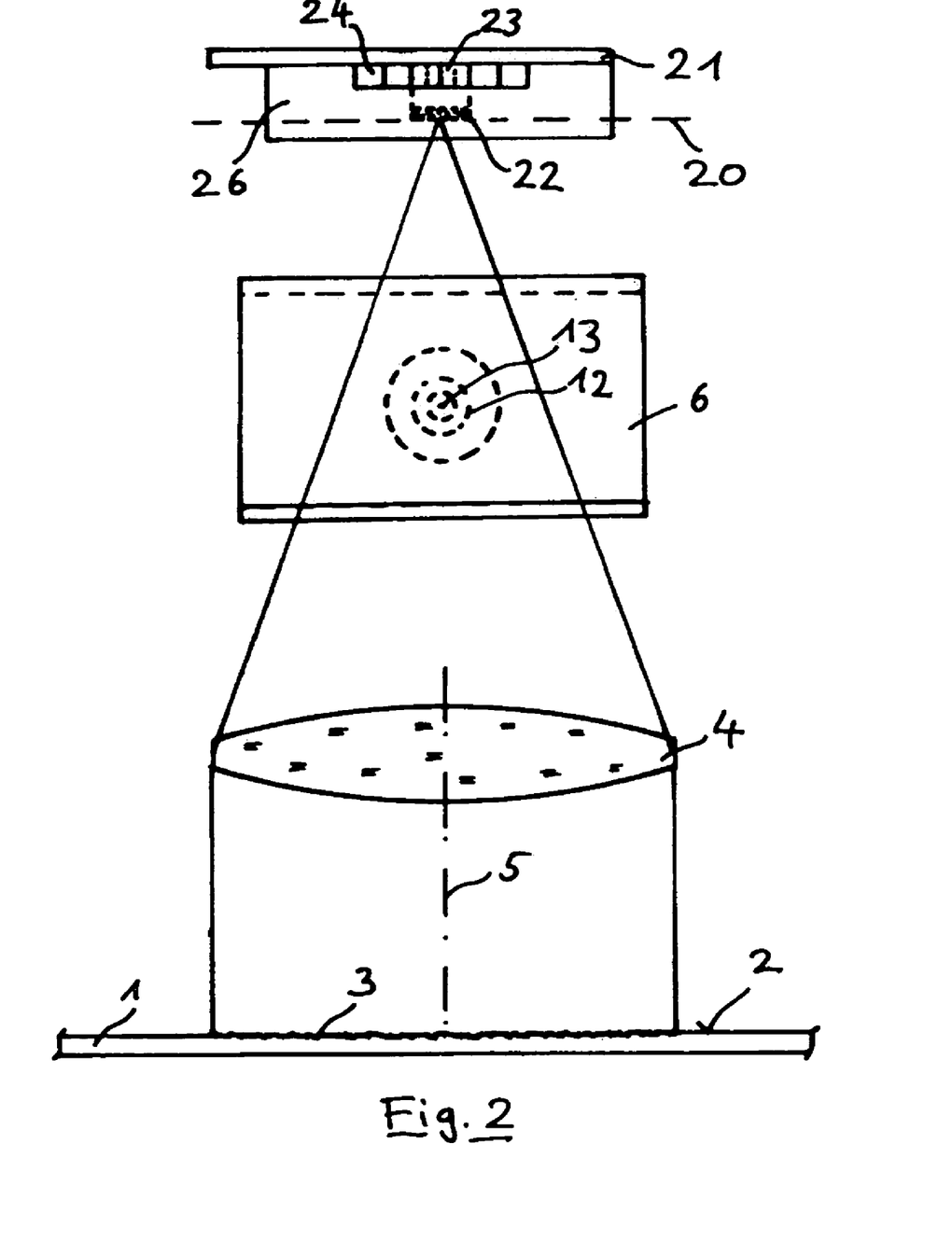
FIG. 2 provides a schematic view of the system of FIG. 1 from a direction orthogonal thereto.

FIG. 2 schematically depicts a view of the system from a direction orthogonal to FIG. 1. As shown in FIGS. 1 and 2, the illuminator beam path images an area on the substrate 1 that is slightly larger than the projection of the field lens 4 on the substrate 1, which will be particularly beneficial when aligning the device, since the investigated section 3 may usually be positioned within the illuminated, bright field by an operator, under visual control, without employing any other alignment aids, and without need for operating the camera 11. In one implementation, if the surface 2 involved is perfectly reflective, it may be necessary to arrange a sheet of a weakly scattering medium, for example, a scattering foil, on the investigated section 3 of the substrate 1 for alignment purposes.

The LED 23 employed for bright-field illumination is arranged on an illuminator board 21 that is schematically depicted in FIGS. 1 and 2. That illuminator board 21 preferably contains other light sources, such as the pair of linear LED-arrays 24, 25, each of which is configured from at least three, collinearly arranged LEDs and may be employed for providing nearly on-axis, dark-field illumination of the investigated section 3.

Those linear LED-arrays 24, 25 are arranged such that their light-emitting surfaces are situated far, in the geometric-optics sense, from the focal plane 20 of the field lens 4, on the side that faces away from the field lens 4, at a distance therefrom that is at least 15% of the focal length of the field lens 4. This preferably yields an imaging geometry where the object-side beam paths of the light sources 24, 25 are no longer parallel, but will be slightly convergent, provided that the surface 2 is situated in front of the image points of the linear LED-arrays 24, 25. In practice, it has been found that a convergent beam path and the associated variations in the angle of incidence on the surface 2 will necessitate a slight realignment of the optical axis 5 relative to the surface 2, assuming that the angle between the optical axis 5 and the surface 2 need not be precisely 90°.

Since both of the linear LED-arrays 24, 25 will be imaged onto the substrate 1 such that their images thereon will be slightly displaced relative to the investigated section 3, it has been contemplated that the linear LED-arrays 24, 25 be arranged on either side of the LED 23. The linear LED-arrays 24, 25 are preferably arranged on the illuminator board 21, and thus outside the focal plane 20 of the field lens 4, without employing any scatter plates. Both the individual LEDs of the linear LED-arrays 24, 25 and the LED 23 are preferably tunable, multicolor LEDs, in particular, so-called RGB-LEDs that incorporate three individual LEDs emitting in the red, green, and blue within a single housing.

The intensities and admixed colors of the emitted light of all LEDs may be tuned by an illumination controller known in the art and will not be described in further detail here. The color of the light emitted by individual LEDs of given linear LED-arrays may vary with their locations in the arrays and with time. However, it is contemplated that, for certain metrological tasks, lookup tables of colorimetric coordinates representing standard illumination conditions be stored in an illumination controller, which will allow more rapid implementation of satisfactory illumination when preparing to record images of the investigated section 3 than would be the case if iterative methods were employed.

The illumination and image-recording beam paths shown in FIGS. 1 and 2 yield the benefit that no astigmatism due to the reflection of the highly divergent beam at the semitransparent, reflective surface 7 of the beamsplitter 6 similar to that which would occur when the beam transits a plane-parallel plate occurs in the camera beam path. Although astigmatism in the camera beam path could be avoidable if the camera's optical axis were to coincide with the optical axis 5 of the field lens and that a beamsplitter cube, instead of a beamsplitter plate, were employed as beamsplitter. In that case, however, color fringes due to chromatic aberration would occur within the beamsplitter cube. Furthermore, the field lens' focal plane would be shifted away from the field lens by approximately the width of the beamsplitter cube, and would thus increase the length of the entire arrangement, as measured along the normal to the surface 2.

Figure 3:
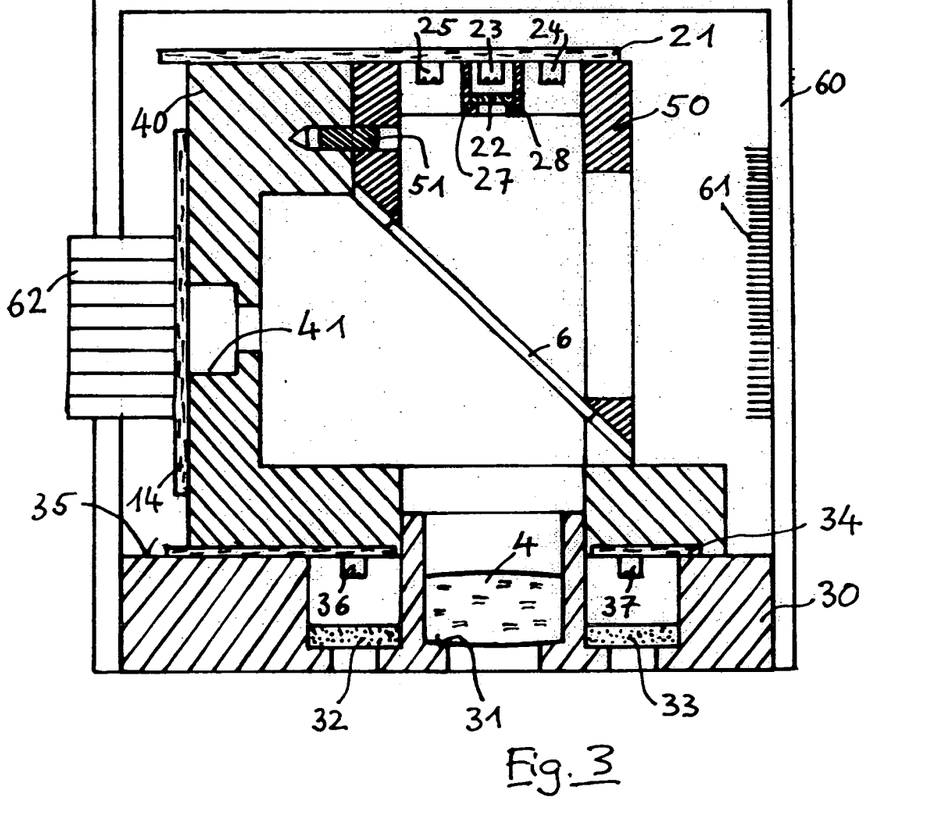
FIG. 3 provides a sectional view of the mechanical layout of a device according to a preferred embodiment of the present invention, where the section is taken along the plane containing the optical axes of the camera and the field lens.

FIG. 3 depicts a sectional view of the mechanical layout of the system according to certain preferred embodiments of the invention, where the section has been taken along a plane containing the optical axes of the camera 11 and the field lens 4. As it will be described in greater detail below, the layout provides the benefit that mechanical alignment of the optical components involved is largely unnecessary, since precision assembly of the entire system has been preordained by substantially minimizing the manufacturing tolerances of the few mechanical parts of the mounts and holders employed. In the case of the embodiment shown in FIG. 3, a front panel 30 supports an optics mount 40, a beamsplitter holder 50, and a housing 60. Although the front panel 30, optics mount 40, and beamsplitter holder 50 are preferably machined from an aluminum alloy, it may be provided that those components 30, 40, 50 are injection molded from plastic materials, which would yield a higher degree of component integration than that of the sample embodiment shown in FIG. 3.

The front panel 30 has a receptacle for the field lens 4, where the mounting surface 31 for the field lens accurately conforms to the contour of its surface that faces the substrate. That mounting surface may be either machined into the front panel 30 or molded onto an injection-molded, monolithic, plastic part. In certain embodiments, it is contemplated that the field lens be cemented thereto in order to mechanically secure it in place. No alignment thereof is necessary. In addition, the front panel 30 has a pair of channels running along the lateral surfaces of the field lens 4, in which a pair of linear LED-arrays 36, 37 in the form of linear light sources situated on an illuminator board 34 are arranged. The sides of the channels that face the substrate are terminated by ground-glass plates 32, 33. The pair of ground-glass plates 32, 33 are intended for the purpose of providing off-axis, dark-field illumination, where the angle between the illumination axis and the optical axis 5 of the field lens 4 exceeds that for the nearly on-axis, dark-field illumination employing the linear LED-arrays 24, 25. The illuminator board 34 is arranged in a recess on the optics mount 40 and held in place thereon by an elastic support. The front panel 30 has an abutment surface 35, on which the optics mount 40 is precisely located employing suitable means known in the art and held in place by fasteners such that it is removable.

The optics mount 40 has a receptacle 41 for the lens 12 of the camera 11. The camera, which is not shown here, is preferably arranged on a camera board 14 that is capable of supporting a schematically depicted heat sink 61, which is in good thermal contact with the outer surface of the housing 60. In the event that temperatures at the installation site require cooling of the camera chip in order to suppress noise, it may be cooled from outside a hermetically sealed and, in particular, dust-tight, housing 60. Adapters that allow assembly without need for alignment are provided on the optics mount 40 and beamsplitter holder 50. These adapters are merely schematically depicted by a pin 51 that accurately aligns the drilled holes in the optics mount 40 and beamsplitter holder 50 visible in FIG. 3 on one another. Mechanical fastening is preferably by means of screws. In one embodiment, the beamsplitter 6 can be either cemented to a mating surface on the beamsplitter holder 50 or spring-loaded against that mating surface by hardware known in the art that are shown here.

Grooves that locate a plurality of baffles 27, 28 and the holder for the ground-glass plate 22 are provided in the beamsplitter holder 50. The linear LED-arrays 24, 25 and LED 23 are arranged on an illuminator board 21 that is held in place by the beamsplitter holder 50. An aperture that allows unimpeded transmission of light rays coming from the light sources 23, 24, 25 and partially reflected by the rear surface of the beamsplitter 6 to a beam stop 61 arranged on the housing 60 is provided on that side of the beamsplitter holder 50 that is situated opposite the receptacle 41 for the camera 11. The beam stop 61 is configured such that very little stray light therefrom reaches the camera 11 arranged in the receptacle 41. Since certain preferred embodiments of the invention contemplate that the beamsplitter is to be mounted in a hermetically sealed, dust-tight housing 60, there is no need in these embodiments for providing means for preventing scattered light from the rear surface of the beamsplitter due to the presence of contaminants thereon, as is contemplated in U.S. Pat. No. 4,561,722A.

In one embodiment, the housing 60 has an electrical feedthrough known in the art that is also preferably dust-tight. The lamps on the illuminator boards 21, 34 and the camera 11 on the camera board 14 are controlled by a central controller that controls all operations related to the illumination of the investigated section 3 and the recording of images, or series of images.

Figure 4:
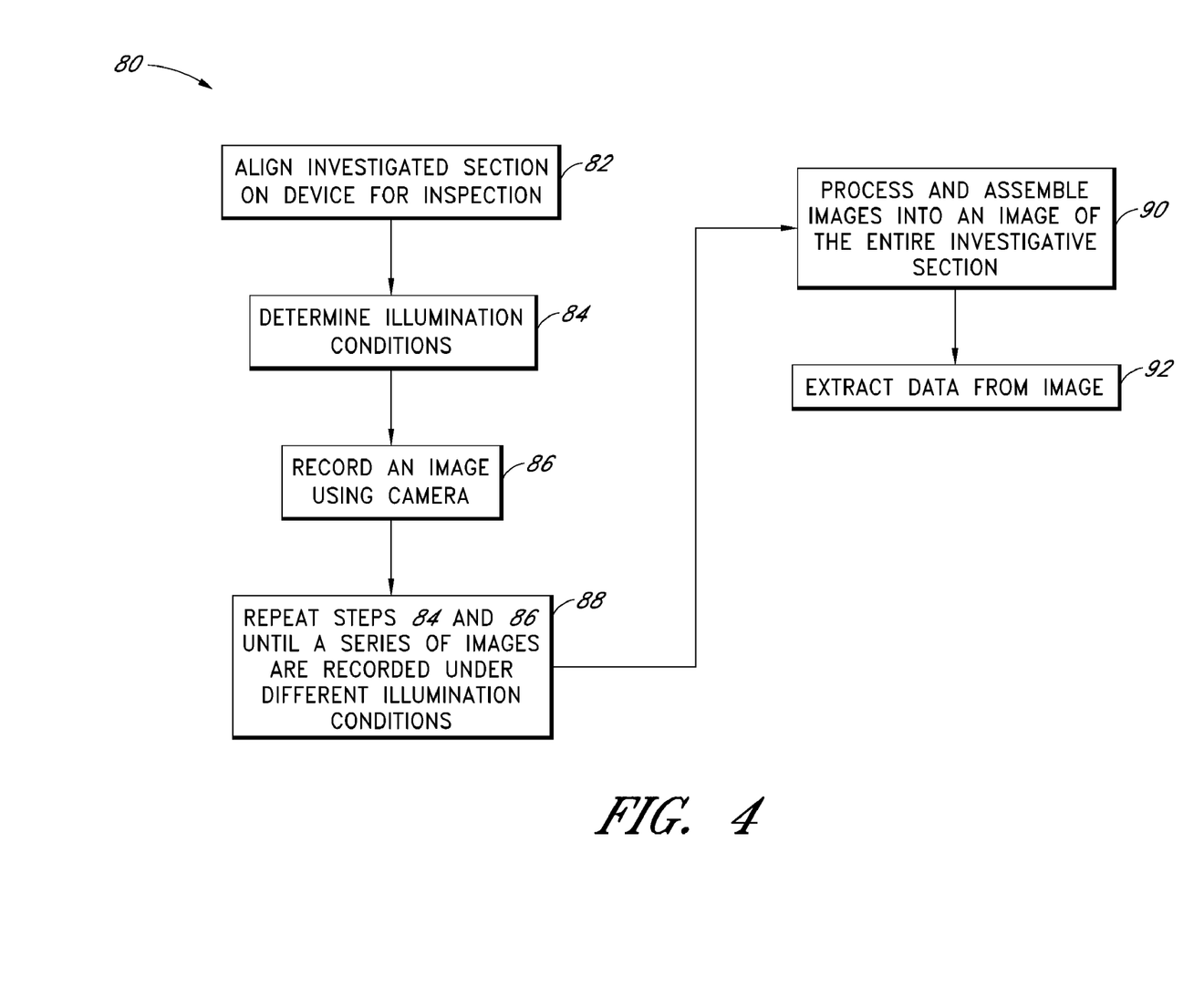
FIG. 4 illustrates a method for optically inspecting a surface employing a device according to one preferred embodiment of the present invention.

FIG. 4 illustrates a method 80 for optically inspecting a surface employing the optical inspection system according to one preferred embodiment of the invention as described above. The method 80 begins with Step 82 in which the investigated section is aligned on device for inspection and continues with Step 84 in which the illumination conditions are determined. In one embodiment, the illumination conditions generally include the spatial arrangements of the light sources, their intensities and/or spectral distributions, and the exposure times. These conditions may be varied from shot to shot. The method 80 further includes Step 86 in which an image is recorded using the camera and Step 88 in which Steps 84 and 86 are repeated until a series of images are recorded under different illumination conditions. In one implementation, the light source used is a LED source that is other than a point source.

In a preferred embodiment, the recorded images are stored in a frame buffer, where each recorded image is characterized by illumination by a group of light sources comprising a fixed number of individual, neighboring light sources from among the numerous light sources, and the light sources have been independently activated and deactivated in sequence. The images are subsequently processed and assembled into an image of the entire investigative section in Step 90 and data is extracted from the resulting image in Step 92. In one implementation, the individual recorded images are processed such that the recorded image having the optimal average brightness will be determined and the associated group of light sources defined as the central bright-field light source for the particular set of investigative conditions involved. In another implementation, processing the images comprises processing exclusively those respective portions of the images of the investigated section that have adequate brightness and contrast. These images are assembled into a single, processable image.

Generally, the method for optically inspecting a surface according to one preferred embodiment is characterized by the fact that one or more images may be recorded employing the camera once the investigated section has been aligned on the device or field lens, where the illumination conditions may be varied from shot to shot, where either a controller executes a stored control program or the illumination conditions and camera settings to be employed are taken from a lookup table by an operator. In some cases, it might happen that only part of the investigated section will be illuminated such that the signal to noise ratios needed for the metrological task at hand and high spatial frequencies will be attained, in spite of the extensive range of illumination conditions available. A series of recorded images should be acquired under differing, respective, illumination conditions and exclusively the processable portions of images filtered out, evaluated, and assembled into an image of the entire investigated section in such cases. Such images that have been assembled from individual partial images in that manner may be processed in order to extract data related to surface textures and/or character recognition employing image-processing software, if demanded by the metrological task involved.

It is provided that the controller of the image-processing computer will receive a signal once the current metrological task has been concluded, or whenever certain characters cannot be unambiguously recognized. In the latter case, it might be provided that the controller will cause the metrological operations involved to be repeated under differing illumination conditions and with the employment of differing image-recording software, until such time as either all characters involved have been unambiguously recognized or one or more characters have been classified as "unrecognizable."

Another method according to the invention for inspecting a surface contemplates that a series of images are recorded by the camera 11 for differing, respective, spatial arrangements of the light sources involved in the focal plane 20 of the field lens 4 and analyzed respecting their overall brightnesses. If the substrate 1 involved has a specularly reflecting surface 2, the arrangement of light sources in the focal plane 20 correlated to the brightest image is specified as "bright-field illumination." The dark-field illumination correlated to that bright-field illumination is composed of an arrangement of light sources that excludes at least those light sources responsible for the bright-field illumination. A light source consisting of numerous, independently controllable, light sources is employed in order to carry out the method. Such light sources could be either an arrangement of numerous LEDs, a micro-mirror array illuminated by a single light source, or an electro-optical spatial light modulator, for example, a controllable, backlit, positive-image, LCD.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

What is claimed is:

1. A device for optically inspecting an investigated section of a specularly or diffusely reflecting surface having at least one light source for providing bright-field illumination that is imaged onto the investigated section employing a telecentric beam path, an electronic camera having a lens that receives part of the light coming from within the investigated section of the surface via a telecentric beam path and transmits the images obtained to a processor, and an electronic controller for controlling the illumination of the investigated section and the operation of the camera, characterized in that the camera-and-illuminator-side beam path has an aspherical field lens whose focal length is less than twice the maximum dimension of the investigated section, and whose projection on the surface to be investigated at least just barely covers the investigated section, where the investigated section is imaged onto the entrance pupil of the lens of the camera by a beamsplitter arranged at an angle of about 45° to the optical axis of the field lens and a light source, other than a point source, whose minimum dimension in the focal plane of the field lens substantially equals twice to ten-times the diameter of the entrance pupil of the lens of the camera is arranged in the focal plane, which is penetrated by the optical axis of the field lens.

2. A device according to claim 1, characterized in that the light source that is other than a point source is configured in the form of a ground-glass plate arranged in the focal plane, symmetrically disposed about the optical axis of the field lens, that is illuminated by a lamp arranged behind the focal plane on that side thereof that faces away from the field lens.

3. A device according to claim 2, characterized in that the lamp is configured from at least one light-emitting, semiconductor diode.

4. A device according to claim 2, characterized in that the lamp comprises three LEDs that emit in the red, green, and blue spectral ranges, respectively, and are independently controllable by the controller such that light of various colors may be generated by additive color mixing.

5. A device according to claim 1, characterized in that at least one, additional, light source in the form of a linear LED-array is arranged on the illuminator side of the field lens, in the vicinity of the optical axis of the field lens, where each such light source is situated behind, as viewed from the field lens, the focal plane, at a distance therefrom equaling at least 15% of the focal length of the field lens, and where said light source is/are controllable by a controller and may be optionally operated either independently of, or jointly with, the light source employed for generating the bright-field illumination.

6. A method for optically inspecting an essentially rectangular investigated section of a specularly or diffusely reflecting surface, employing a device according claim 1, that characterized by the following processing steps:

preparing a series of recorded images and storing the recorded images in a frame buffer, where every recorded image is characterized by differing, intense illumination by the light source that is other than a point source;

processing the individual recorded images stored in the frame buffer and processing circuitry such that, from among those recorded images, exclusively those respective portions of the images of the investigated section that have adequate brightness and contrast will be selected for further processing and assembled into a single, processable image; and processing the assembled image of the investigated section, employing software that will automatically accomplish the inspection task involved.

7. A method for optically inspecting an essentially rectangular investigated section of a specularly or diffusely reflection surface, employing a device according to claim 1, characterized by the following processing steps:

preparing a series of recorded images and storing those recorded images in a frame buffer, where each recorded image is characterized by illumination of the investigated section employing the LED as the light source that is other than a point source and the linear LED-arrays, and by differing ratios of the intensity of the LED to the intensities of the linear LED-arrays;

processing the individual recorded images stored in the frame buffer and processing circuitry such that, from among those recorded images, exclusively those respective portions of the images of the investigated section that have adequate brightness and contrast will be selected for further processing and assembled into a single, processable image; and processing the assembled image of the investigated section, employing software that will automatically accomplish the inspection task involved.

8. A method for aligning a device according to claim 3, characterized in that the intensity of the LED employed as the light source that is not a point source is set to its maximum tolerated value and the user sets up the device, under visual control, such that the section of the surface that is brightly illuminated by the LED encompasses the investigated section in order to mechanically align the device on an essentially rectangular investigated section.

9. A method for aligning a device according to claim 4, characterized in that the intensity of the LED employed as the light source that is not a point source is set to its maximum tolerated value and the user sets up the device, under visual control, such that the section of the surface that is brightly illuminated by the LED encompasses the investigated section in order to mechanically align the device on an essentially rectangular investigated section.

10. A method for aligning a device according to claim 5, characterized in that the intensity of the LED employed as the light source that is not a point source is set to its maximum tolerated value and the user sets up the device, under visual control, such that the section of the surface that is brightly illuminated by the LED encompasses the investigated section in order to mechanically align the device on an essentially rectangular investigated section.

11. A method for optically inspecting an investigated section of a specularly or diffusely reflecting surface, employing a device having numerous, identical, light sources situated in the focal plane of a field lens that are imaged onto the investigated section, employing a telecentric beam path, an electronic camera having a lens that receives part of the light coming from within the investigated section of the surface via a telecentric beam path and a beamsplitter and transmits the images obtained to a processor, along with an electronic controller for controlling the light sources situated in the focal plane of the field lens and the operation of the camera, and a frame buffer and processing circuitry, characterized by the following processing steps:

preparing a series of recorded images and storing the recorded images in a frame buffer, where each recorded image is characterized by illumination by a group of light sources comprising a fixed number of individual, neighboring, light sources from among the numerous light sources, and the light sources have been independently activated and deactivated in sequence;

processing individual recorded images stored in the frame buffer with processing circuitry such that recorded image having an optimal average brightness will be determined and the associated group of light sources defined as the central bright-field light source for the particular set of investigative conditions involved;

classifying the groups of light sources into bright-field light sources that include at least the central bright-field light source and, optionally, light sources that are immediately adjacent thereto, and dark-field light sources that are arranged about the bright-field light sources, at distances therefrom equaling at least the lateral dimension of a light source;

recording a series of images of the investigated section, where the respective illumination conditions employed in recording the images involved range from strictly bright-field illumination, through combined bright-field/dark-field illumination, to strictly dark-field illumination; and processing the recorded images of the investigated section using software that will allow automatically accomplishing the inspection task involved.

\* \* \* \* \*